United States Patent [19]

Propp et al.

[11] Patent Number: 5,538,132
[45] Date of Patent: Jul. 23, 1996

[54] GUARD STRUCTURE FOR SHARPS

[75] Inventors: Donald J. Propp, Dewitt; Jerry H. Roberts, Okemos, both of Mich.

[73] Assignee: Tri-State Hospital Supply Corp., Howell, Mich.

[21] Appl. No.: 82,474

[22] Filed: Jun. 28, 1993

[51] Int. Cl.$^6$ .......................... B65D 85/24; A61B 17/06
[52] U.S. Cl. ..................... 206/365; 206/63.3; 206/350; 206/818
[58] Field of Search ................. 206/63.3, 365, 206/350, 818, 813, 366

[56] References Cited

U.S. PATENT DOCUMENTS

| | | | |
|---|---|---|---|
| 2,246,984 | 6/1941 | Palmer | 206/813 X |
| 3,727,658 | 4/1973 | Eldridge, Jr. | 206/818 X |
| 3,861,521 | 1/1975 | Burtz | 206/63.3 |
| 3,944,069 | 3/1976 | Eldridge, Jr. | 206/350 |
| 4,008,802 | 2/1977 | Freitag | 206/63.3 |
| 4,013,109 | 3/1977 | Sandel | 206/63.3 |
| 4,254,862 | 3/1981 | Barratt | 206/63.3 |
| 4,637,513 | 1/1987 | Eldridge, Jr. | 206/370 |
| 4,758,229 | 7/1988 | Doerschner | 206/365 X |
| 4,859,515 | 8/1989 | Pothetes | 206/365 X |

*Primary Examiner*—Bryon P. Gehman
*Attorney, Agent, or Firm*—C. J. Fildes & Co.

[57] ABSTRACT

A compact, low-cost laminar disposable package and manufacture therefor, for use in surgical procedures. Such packages are used by medical personnel as convenient magnetic receptacles and use stations to receive medical sharps at point of use and, upon closure, the packages guard against chance loss of needles and other sharps while also guarding against injuries incidental to the disposal of surgical-medical sharps.

4 Claims, 3 Drawing Sheets

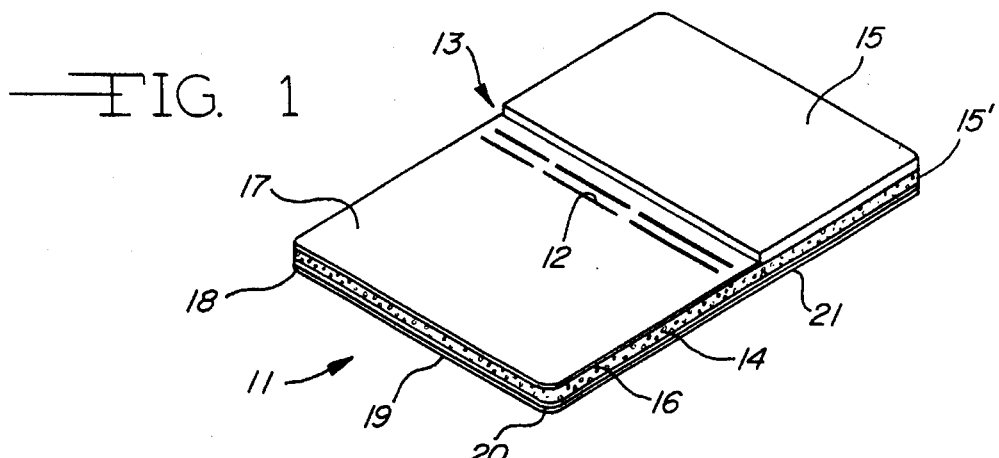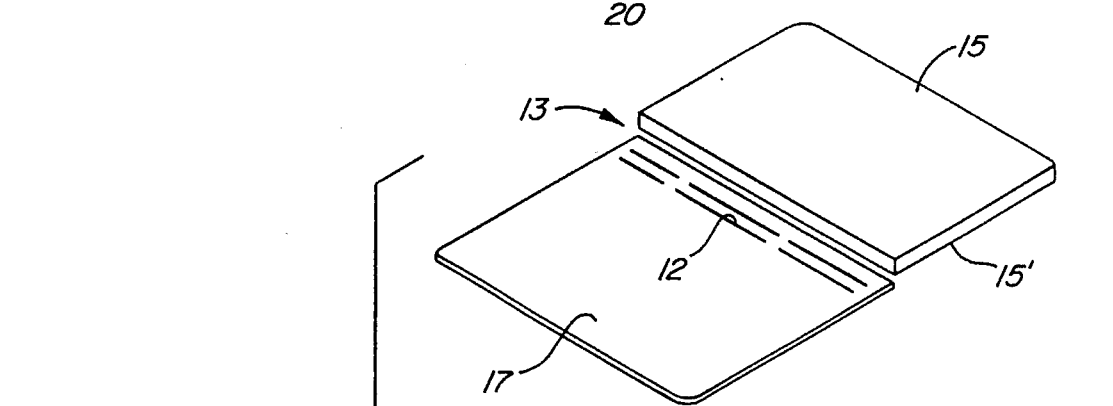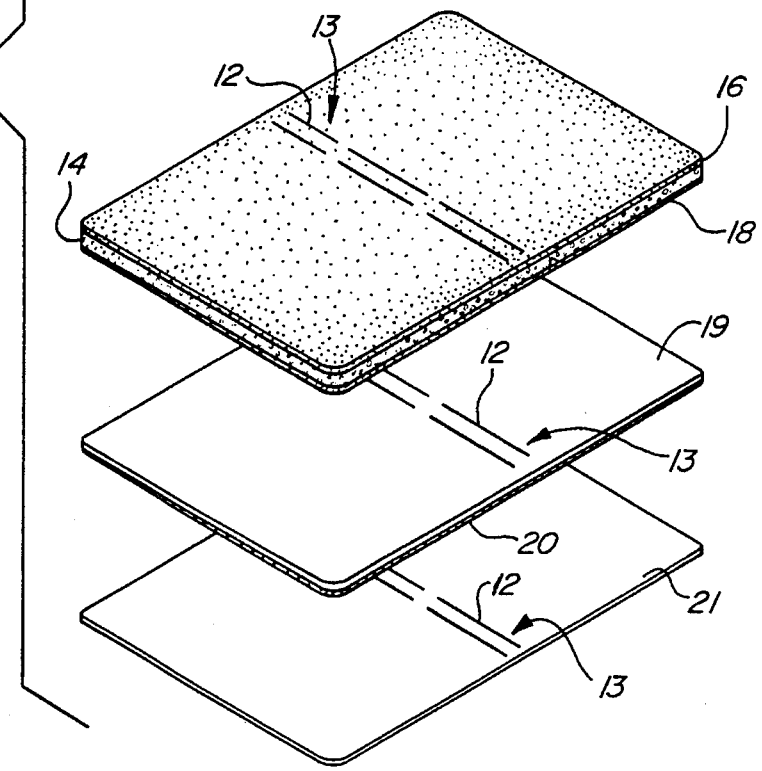

GUARD STRUCTURE FOR SHARPS

The present invention is directed to a discardable package structure for medical and surgical sharps such as throw away suture needles, disposable scalpel blades and the like which are used in suturing and other surgical procedures and are considered dangerous because of the sharpness, odd shapes, and exposure of personnel to possible diseased blood and tissue. Such sharp objects as needles and other small implements as discardable blades used in surgery require temporary protected retention during use and, in the instance of throw away sharps, there is an ever present need to consider safe envelopment in compact form to serve the users of the instruments while surgery is proceeding, allowing safety envelopment and accounting for the sharps when the procedures are complete, and safe handling for discard. Accordingly the presently described structures are small enough to be used on a surgical instrument tray or in a stand-alone position to provide a safe and accessible temporary resting location during usage and to provide a safe disposal wrapper which packet or package is then conveniently deposited in a sharps disposal container.

BACKGROUND OF THE INVENTION

While convenience during instrument usage is facilitated by the size and construction of the present invention in accounting for the instruments, the advantage for after-surgery procedures in accounting for, locating and handling of the sharps is in the time saved and safety to surgery, nursing, and disposal personnel. The invention is embodied in a laminar flat profile construction having a thin magnetic strip permanently adhered to a foam core or carrier which projects beyond the magnet strip and the projecting foam core or carrier portion is foldable on weakened fold lines to close on the magnet strip and be adhered to the exposed magnet face by the same permanent adhesive strip which holds the magnet in place. The foam carrier strip or pad deforms selectively over objects such as surgical and medical sharps placed on the magnet surface and, upon folding the carrier strip, establishes a permanent bond to the magnet substrate. Exposure or activation of the adhesive is achieved by simple stripping away of a release coated cover sheet from the adhesive covered extended portion of the foam core or carrier sheet.

The structure of the present inventive unit is generally flat having an open face dimension proximate to the size of an ordinary business card so that the structure is at home comfortably secured to an operating tray, to the wrist of a surgeon, or to a surgical drape at or adjacent the operation situs.

While the invention embraces the laminar unit, it embodies and extends to the procedures for economical manufacture of the laminar unit which assures a safe uniform product which itself is subjected to a sterile manufacturing procedure and guarded and made readily accessible to surgical and medical personnel.

Accordingly the principal object of the invention is the presentation of a laminar sharps disposal packet that is relatively compact or small, is easily used, and is closable over the sharps while providing location control for the sharps and surgical implements adjacent the situs of use.

Another object is to teach the new, useful and unobvious economical manufacture of the presently described laminar sharps disposal packet.

Still other objects include resultant economies and substantial extension of improved surgical instrument inventory and improved elimination of chance injuries.

Those skilled in the surgical procedures, doctors, nurses, technicians and others comprising a surgical team will readily perceive other and obvious advantages in elimination of clutter and instrument control and handling economies.

DESCRIPTION OF RELATED ART

There is a considerable body of art dedicated to the packaging and handling of surgical and disposable sharps and the closest known patented structures are represented in the work of Burtz in United States Letters Patent No. 3,861,521 which presents a disposable suture organizer for holding and presenting a selection of suture and suture needles in plural individual packets of transparent wallet-like appearance and including plural magnet bars to retain the suture needles after use. The Burtz structure assists in counting needles and in the segregation of types and sizes of sutures and needles. Permanent and guarded disposal is not considered in this reference for the surgical sharps.

In the United States Letters Patent No. 4,013,109 to Sandel a disposable container is proposed which is hinged in a rigid or non-deformable outer encasement and in which magnetic means cover the interior floors of the case to retain magnetically attracted instruments placed in the case. The Sandel device includes a magnetic grooved floor adhesively connected within the fitted hinged parts of the container, the grooves facilitating the handling of instruments as suture needles.

Previously, the United States Letters Patent Nos. 3,727,658 and 3,944,069 of Eldridge had proposed structures for disposable surgical instruments which, in the latter patent, included a pair of guideable penetrable foam plastic pads and a backing element for each pad with a hinged element allowing movement of the pad elements to close, one on the other. Included was a pressure sensitive coating which covers one exposed pad face but not the other pad face. Also included was an outer protective lamination or strippable cover sheet over the adhesive faced of the pads. Magnets could be imbedded in the adhesive faced of the pads to facilitate retention of instruments placed thereon.

As understood, the prior art devices do not propose a completely laminar structure in which a single foamed resin pad provides a base upon which a magnetic plate is permanently adhered and which, with laminar sheet elements, permits a compact closing of the planar structure upon the magnetic plate sealing the sharps against injury to personnel and readying the package for disposal. In addition the present selected construction of the planar laminar devices is complemented by the present process for manufacture made possible by the construction and capable of high productivity at economical cost. The size of the finished units permits the devices to be easily carried and stocked for usage by doctors, nurses and technicians. The resultant package provides a handy work mate and solves substantial problems at surgical sites.

Other inventive differences will be appreciated as the description proceeds and the simplicity of the structure and its manufacture are appreciated.

SUMMARY OF THE INVENTION

The convenience structure for sharps disposal is a relatively small and planar laminar package built up of successive layers of materials from a rectangular and planar core or carrier sheet of foamed plastic material. Substantially one half of the length of the core or carrier sheet is covered with a thin, rectangular magnet of oriented magnetic particles such as magnetizable ferrous polarity oriented fragments in a plastic matrix and the thin, bendable magnet is secured to the foam core by a sheet or layer of permanent adhesive material which overlaps the upper surface of the core or carrier sheet. The portion of the permanent adhesive sheet left exposed by the placement of the magnet is covered by a removable liner sheet which extends slightly beyond the carrier or core sheet and otherwise rests on the upper surface of the permanent adhesive. The removable liner extends substantially to the edge of the magnet. A tab portion of the removable liner extends slightly over the edge of the magnet adjacent the removable liner to facilitate selected removal. Beneath the carrier or core and adhered to the bottom side of the foam core (FIG. 1) is a sheet of permanent pressure sensitive adhesive covered by a removable liner. Thus a portion of the adhesive sheet extending beyond the projected position of the magnet is coated with permanent adhesive and the permanent adhesive is in turn covered by a removable liner of semi-rigid material which may be an extension of the adjacent removable bottom liner but is separated therefrom by a die cut. Scoring of fold lines is provided to form folds or creases for the laminar structure. This simple laminar structure may be imprinted on the liner outer surfaces with instructions for use, the bottom removable liner is removable at its scored approximate mid-point to expose an adhesive surface making the laminar packet attachable to an instrument tray, clothing, wrist of a surgeon or technician, or on any selected surface including surgical drapes and equipment for convenience of access to the upper exposed magnet surface for magnetic retention of sharps in use or in discard during surgical procedures. Upon completion of use, the upper removable liner is removed exposing the upper permanent adhesive, and the foam core, with its laminar layers, is thereupon folded at the pre-established fold or crease and over the edge of the magnet. It may be pressed against the upper surface of the magnet with the activated permanent adhesive over any included magnetically retained sharps and the package is ready for safely picking up and disposing at a sharps disposal station. The construction will be better understood by reference to the attached drawings. While capable of construction by various manufacturing procedures, the preferred procedure is described which is most adaptable to low cost production.

The procedure shown for fabricating the disposal package is vastly simplified and complements the laminar construction. All materials are amenable to strip application from rolls of precut and pre-positioned materials. These materials are flowed from the rolls in a synchronous parallel manner with tangential merging to form the rectangular laminar construction seen in the finished disposal product. Imprintation of the liner pieces may be applied to the liner material on the rolls before flowing the material and securing the materials in the necessary sequencing. Necessary scoring and slitting of the webs of liner material and trim with die cutting occurs on the flow path of the laminant and lamination transfer proceeds with recovery wind up and die cut salvaging. The completely assembled and precision sized product packages exit from the described operations and may be sterilized as required. It will be appreciated that the entire sterilization process may be performed under required sterilization procedures and packaged and wrapped as needed.

BRIEF DESCRIPTION OF THE DRAWINGS

In the Drawings FIG. 1 is a perspective view of the surgical sharps convenience holder and disposal structure in planar laminar form with the thin magnet means the uppermost exposure surface adjacent the upper and removable liner sheet and indicating the sequence of the layers of material as stacked in relation to the foam core or carrier.

FIG. 2 is a perspective exploded view of the structure shown in FIG. 1 and sandwiched over the foam core or carrier the foam core is coated with permanent adhesive on both top and bottom surfaces.

DESCRIPTION OF THE PREFERRED EMBODIMENT

Figure 3:
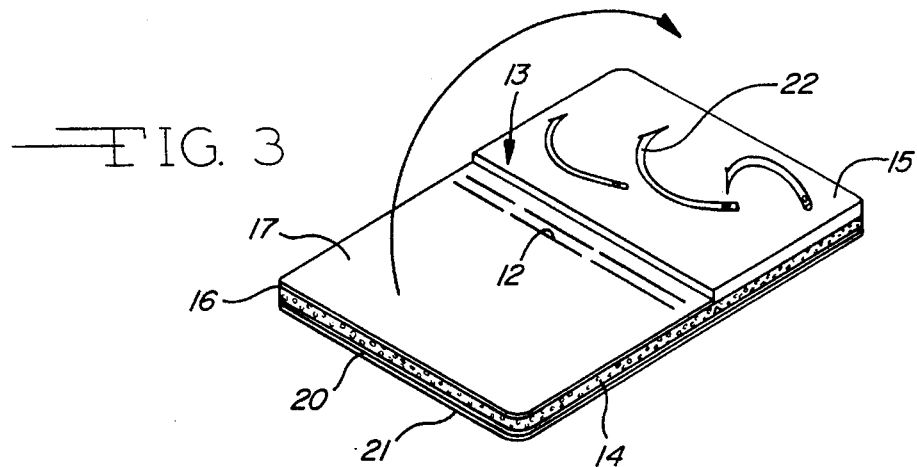
FIG. 3 is a perspective view of a functioning complete convenient package in accord with the present invention and indicating the placement of instruments shown as suture needles retained on the exposed upper surface of the magnet portion of the planar laminar package and showing the folding direction for the package as hinged on the scoring lines which fold over occurs after the removal of the upper liner to expose the adhesive layer therebeneath. As shown, this is the use position before closure for disposal.

The disposal structure 11 of the present invention, as seen in FIG. 1, comprises a laminar, flat package 11 built upon a plurality of relatively flat elements, each contributing to the assembly, and scored 12 so as to be selectively flatly folded over on a living hinge support 13 provided by a core or carrier piece 14 or pad of flat stock such as a relatively high density foamed resin material (for example, polyurethane) which has an ability to resist sharps penetration and to crush over and around irregularities to a firm, flat surface, such as the base presented by the relatively rigid, thin, and somewhat flexible magnet 15. The magnet 15 is permanently adhered at the lower face 15' of the magnet 15 to one half of the generally rectangular core piece 14. This is achieved by an intermediate permanent adhesive sheet 16 positioned between the foam core piece 14 and the lowermost flat surface of the magnet 15', as seen in FIG. 1. The sheet of permanent adhesive 16 extends beyond the width of the magnet 15, and fully registers against the uppermost face of the mated foam core or carrier 14. A cover liner 17 of release paper extends from the magnet 15, and as will be seen, the cover liner 17 can be removed from the permanent adhesive 16 by simply peeling-away the cover liner 17. Such peeling away at the release surface prepares the foam core liner 14 to be folded over the edge of the magnet 15 on the hinge 13 (which folding is required preliminary to disposal of the unit 11) and sharps placed on the magnetic surface are then blanketed by the foam core piece, and the permanent adhesive 16 then grips the exposed upper surface of the magnet 15, gripping and enfolding the sharps placed thereon. Upon selected removal of the cover liner 17, it will be appreciated that all of the laminations beneath the magnet move upon folding at hinge 13 to permit closure and permanent sealing of any instruments or sharps placed on the magnet 15, as the permanent adhesive surface of the sheet 16 closes against items on the upper face of the magnet 15.

Beside the cushion of the folded core piece 14 a lower adhesive sheet (preferably permanent) 18 is secured to the bottom of the core piece 14 in registry thereagainst. The lower adhesive sheet 18 thus bonds itself to the next adjacent laminate, a registering piece of tag board 19. The tag board 19, on its lower surface, includes an adhesive pressure sensitive laminate 20. A backing of release paper 21 is the bottom-most laminate, and it is registrably located beneath the adhesive, pressure sensitive laminate 20. It is thus selectively removable from the adhesive layer 20 by peeling. As will be noted, the removal of part or all of the release paper cover 21 permits the disposal structure 11 to be adhered to substantially any surface, including surgical drapes, the body of the patient, the back of a surgeon's hand and even against adjacent furniture, to support the sharps and instruments on the exposed surface of magnet 15 for convenience of use, for instrument accounting, and for disposal. The living hinge support 13, achieved by the scores 12 penetrating all layers (except the magnet 15) of the laminated package 11, allows folding effective closure of the package for disposal.

In the FIG. 2 the laminar structure 11 of FIG. 1 is exploded to best show the relationships of the structural parts. The perforations 12 forming the living hinge 13 which permits the folding over of the flat structure 11 is also best understood in this view.

In FIG. 3 the structure of FIG. 1 is seen with sharps 22 (shown as suture needles) resting upon the magnetic face or stage formed by the magnet 15. The base of the structure 11 can be adhered to substantially any surface, at positions ranging from horizontal to vertical, and against substantially any material, including human skin, for convenience in use at an operating site by activating the pressure sensitive adhesive by removal of the release backing paper 21 thus exposing the adhesive undersurface, as shown. The force arrow in the FIG. 3 indicates the closure of the package 11 when the package 11 is ready for disposal with cushion coverage of instruments, shown as sharps 22.

Figure 4:
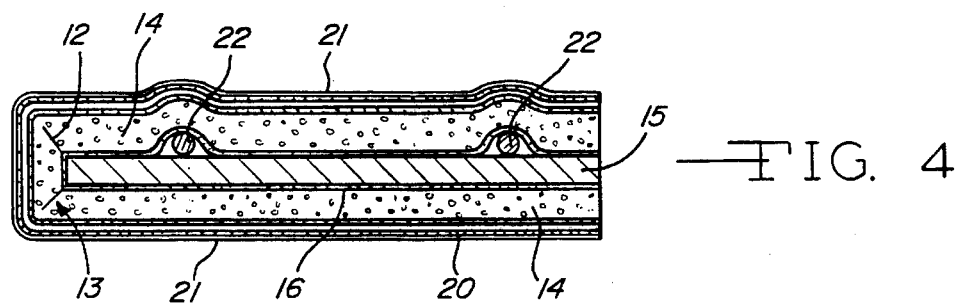
FIG. 4 is a side elevation view of the convenience structure of FIG. 3 after removal of the upper liner and sealing closure of the permanent adhesive over and around the sharps of the suture needles and against the magnet face and indicating the final and closed package ready for disposal and with the sharps completely covered.

FIG. 4 provides a somewhat enlarged side elevation of the unit 11 upon closure over the instruments or sharps 22.

Figure 5:
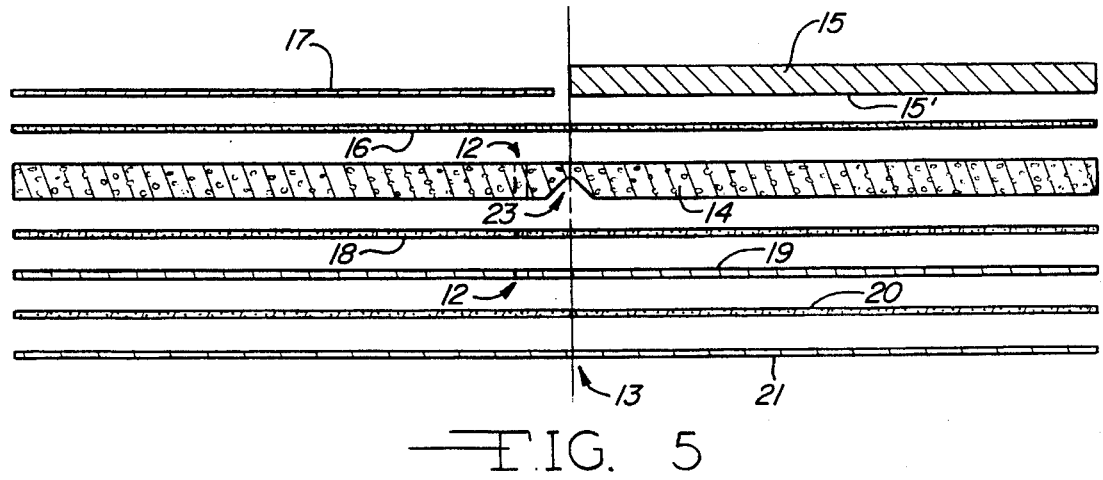
FIG. 5 is a somewhat enlarged side elevation view of the laminations forming the planar package of FIG. 1 in its preferred form and indicating the fold and die cuts adjacent the fold plane.

In the FIG. 5 a somewhat schematic representation of the laminate stock is indicated describing the notching 23 of the foam core 14 adjacent the fold line 13 to achieve the fold over capability adjacent the edge of the magnet 15. The perforations at 12 are indicated through the laminations, as shown.

As will be appreciated, the manufacture of the package 11 may be achieved in a variety of ways, as for example, stacking combinations of the laminations in selected sequences, bottom to top. Such approaches, while useful, are scarcely economic, and the preferred method of manufacture is best accomplished as schematically represented in the FIGS. 6 and 7, in view of the adhesives required and the desireability to maintain uniformity of package size, speed of manufacture, and minimization of waste material. Considerable economy is experienced by the illustrated procedures in which rolls of stock are synchronously and registrably superimposed with transfer webbing as required for each lamination and the released material between adjacent layers is reclaimable as selvedge. The whole structure is simply sized and perforated or scored after achievement of registering assembly, as shown. The result is an extremely rapid manufacture which is amenable to sanitization and sterilization, needing minimum manual attention, and adaptable to well known wrapping and packaging in stacked and wrapped groups, not shown.

Figure 6:
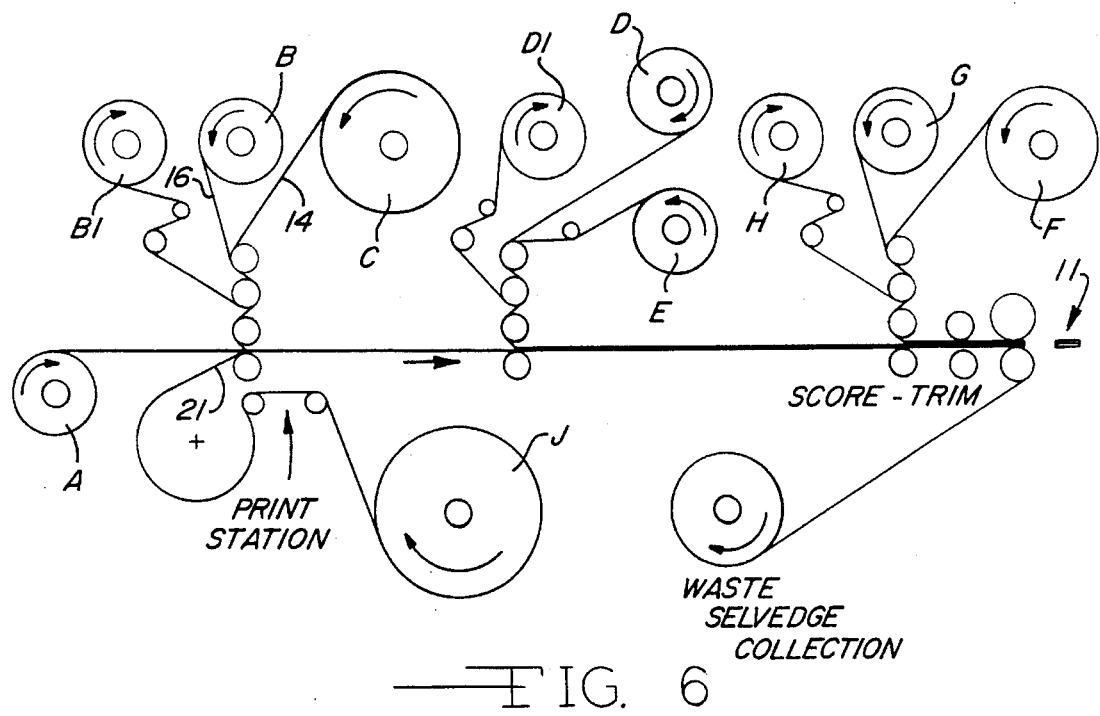
FIG. 6 is a schematic side elevation view of the process, operations and structure utilized in the preferred procedure of manufacturing the convenience package or packet in the description which follows.
Figure 7:
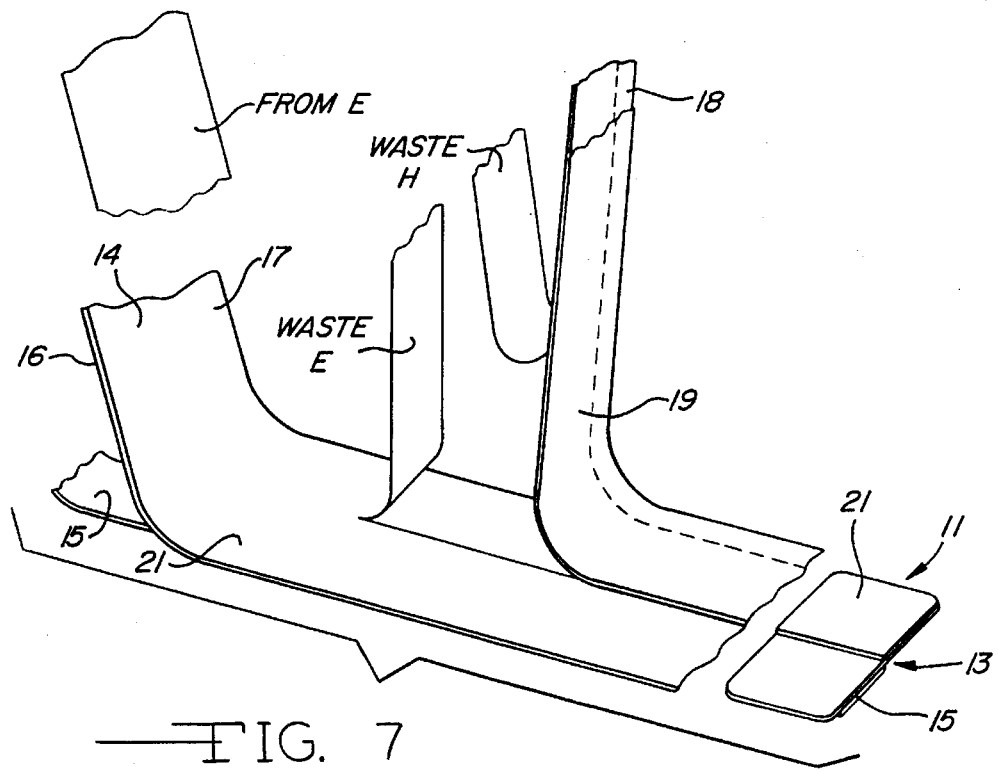
FIG. 7 is a schematic fragmented perspective view of the preferred manufacture of the present invention and indicating the merging of the lamination material to achieve a most economical fabrication of the planar packets and for high production thereof. The die trimmed and scored end product is indicated.

The FIGS. 6 and 7 best illustrate the preferred manufacture of the laminar units 11, as previously described. The magnets 15 are made in strips of ferromagnetic particles in a resin matrix in which the magnetic polarity is transverse to the major planar surfaces. Such magnetic material is available from various sources in rubber and flexible resin materials and also from Indiana Steel Products Divison of Indiana General Corporation, Valparaiso, Ind. under the tradename Indox. It is extruded and cut to wafer form and is prepared in rolls of thin stock. By utilizing the magnets thus available, and in building the laminar construction 11 with alternate adhesive webbing sheets, the desired construction can be automated to the point of automatic manufacture where the laminations are synchronously present from rolls to the surfaces, as desired, and finally merged, with or without transfer, as indicated, and is die cut to size, scored or perforated as desired, and ejected for packaging and stacking. The manufacturing procedure, as described, is also amenable to simultaneous printing on the outside liners or covers for guidance to users, and for coding, dating and record keeping, as will be seen.

Commencing with roll A of magnetic material the magnetic strip from which the magnets 15 are cut travels from the roll A and is guided onto the removable outer liner material (which is printed with instructions and identity information) from the roll J. At the point of entry to the assembly and fabrication, the magnet material on the liner material is removably bonded to the removable liner from the roll J. The foam core material on roll C is guideably conveyed and receives, by transfer, the permanent adhesive sheet from roll B, and the foam core plus the added permanent adhesive is transferred to the magnetic material which is thereupon adhered to the foam core by the permanent adhesive. Then, from roll D, the repositionable (non-permanent) adhesive is travelled over a roll delivering a removable liner from roll E and process liner residue is received by a roll E. The removable liner from roll E is continuously conveyed to the web of B, C, and D and E and joins the semi-rigid outer cover material 21 for final die cutting, scoring, and slitting. The continuance of the movement of the web rolls B, C and D, E thus receives the semi-rigid material (outer cover 21) after receiving a coating of the web of permanent adhesive from roll G. The roll H picks up the residue paper liner, and transfer of the lamination from roll G occurs at the point of contact where the residue paper runs over the contact roller. Then the waste or selvedge is trimmed from the laminar package 11 and the nipping dies cut and trim the unit 11 to size consecutively, but in continuous motion, and the finished units 11 are completed and are subjected to final sterilization and sterile packaging.

By reference to the FIG. 7 the sequence of presentation is simplified to visualize the order of presentation from the rolls C (foam core 14) applied with permanent adhesive 16, to the removable paper liner from roll J with stripping away of the web waste E. The magnetic material forming the magnets 15 is thus permanently adhered to the foam core 14.

With further progress from left to right in the FIG. 7 the transfer of repositionable adhesive from roll D is applied to the removable liner from roll E. Finally, the semi rigid material from roll F, with permanent adhesive applied from roll G, is delivered to the product sandwich as indicated. The selvedge material is salvageable, and in some instance, may be reused for repeated adhesive transfer purposes. Printing explaining the closing of the hinged 13 portion of liner 17 the structure 11 on the needles and instruments for disposal is applied to the portions shielding the fold-over.

In use the packages are convenient in size for use by medical personnel, in offices, hospitals and laboratories and the price is a fraction considering the advantages in time and improvement in the handling techniques for surgical sharp throw aways.

Having thus described our invention, those persons skilled in the art will appreciate improvements, modifications, and changes. Such improvements, modifications and changes are intended to be included in the present invention, limited only by the scope of the following claims.

We claim:

1. A convenience structure for sharps disposal comprising: a flat rectangular planar laminar body having a foam core piece, an upper sheet of permanent adhesive and also a lower sheet of permanent adhesive, a thin wide bodied magnet adhered to said upper sheet of permanent adhesive and covering substantially one half of said foam core piece with a first edge along a free edge of said laminar body, an upper removeable release paper liner covering the remainder of said upper sheet of permanent adhesive; a semi-rigid tag board adhered to the foam core piece by said lower sheet of permanent adhesive, said tag board having an adhesive pressure sensitive laminate coated lower surface for adhering said structure to a supporting surface; a lower-most removeable release paper liner adhered to said adhesive pressure sensitive laminate and selectively removeable from said tag board by peeling; and said rectangular planar laminar body also having a hinge defined by parallel scores penetrating all layers of said laminar body adjacent an edge of said magnet opposite said first edge whereby said foam core piece is smoothly and hingedly foldable over said magnet and, upon removal of said upper liner sheet, said foam core, piece may be selectively and permanently bonded to said upper surface of said magnet by said permanent adhesive to firmly blanket sharps retained on the exposed surface of said magnet.

2. A convenience structure for sharps disposal preparation in accord with claim 1 whereby said magnet is a ferrous magnetizable and polarized material in a thin plastic matrix, the poles of said magnet oriented transversely of the upper and lower broad surfaces of said magnet.

3. A convenience structure for sharps disposal preparation in accord with claim 1 further including an indentation defining a fold line adjacent a longitudinal edge of said magnet adjacent and parallel to said scores, said scores facilitating removal of said release paper liners and positioned to fold said structure with a slight overlap of said magnet.

4. A convenience structure for sharps disposal preparation in accord with claim 1 in which the rectangular planar laminar body is slightly longer than twice the width of said magnet and said thickness of said laminar body being about three times the thickness of said magnet.

* * * * *